(12) United States Patent
Hoeffler

(10) Patent No.: US 6,913,880 B1
(45) Date of Patent: Jul. 5, 2005

(54) METHOD FOR DETERMINING TRANSCRIPTION FACTOR ACTIVITY AND ITS TECHNICAL USES

(75) Inventor: Warren Hoeffler, San Carlos, CA (US)

(73) Assignee: XGene Corporation, Burlingame, CA (US)

( * ) Notice: Subject to any disclaimer, the term of this patent is extended or adjusted under 35 U.S.C. 154(b) by 0 days.

(21) Appl. No.: 09/622,703

(22) PCT Filed: Oct. 6, 1999

(86) PCT No.: PCT/US99/23277
§ 371 (c)(1),
(2), (4) Date: Aug. 21, 2000

(87) PCT Pub. No.: WO00/22167
PCT Pub. Date: Apr. 20, 2000

Related U.S. Application Data

(60) Provisional application No. 60/103,803, filed on Oct. 9, 1998.

(51) Int. Cl.[7] .......................... C12Q 1/68; C12N 15/00; C12N 15/63; C12N 1/20; C07H 21/04
(52) U.S. Cl. ...................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1
(58) Field of Search .......................... 435/6, 91.1, 91.2, 435/69.1, 252.3, 883; 536/24.3, 23.1, 23.4, 23.5, 24.31; 935/6, 1, 19; 436/518

(56) References Cited

U.S. PATENT DOCUMENTS

| | | | | |
|---|---|---|---|---|
| 5,851,772 A | * | 12/1998 | Mirzabekov et al. | 435/6 |
| 5,854,020 A | * | 12/1998 | Hodgson et al. | 435/69.1 |

FOREIGN PATENT DOCUMENTS

| | | | | |
|---|---|---|---|---|
| EP | 0 441 483 A2 | 8/1991 | ........... | C12N/15/12 |
| EP | 0 628 817 A1 | 12/1994 | ........... | G01N/33/53 |
| FR | 2 760 025 A | 8/1998 | ............ | C12Q/1/68 |
| WO | WO 90/05745 | 5/1990 | ........... | C07K/13/00 |
| WO | WO 96/28571 | 9/1996 | ............ | C12Q/1/68 |

OTHER PUBLICATIONS

Gansz et al., "Gene product dsbA of bacteriophage T4 binds to late prommoters and enhances late transcription", Molecular and General Genetics, vol. 225, pp. 427–434, 1991.*

Michelotti et al., Mulitple Single–Stranded CIS–Elements are Associated with Activated Chromatin of the Human C–MYC Gene in vivo, Molecular and Cellular Biology, vol. 16, No. 6, Jun. 1996, pp. 1656–2669.

Evans et al., S1–Hypersensitive Sites in Eukaryotic Promoter Regions, Nucleic Acids Research, vol. 12, No. 21, 1984, pp. 8043–8058.

Stewart et al., Rapid Induction of c–fos Transcription Reveals Quantitative Linkage of RNA Polymerase II and DNA Topoisomerase I Enzyme Activities, Cell Press, vol. 60, Jan. 12, 1990, pp. 141–149.

Wang and Roeder, DNA Topoisomerase I and PC4 Can Interact with Human TFIIC To Promote Both Accurate Termination and Transcription Reinitiation by RNA Polymeras III, Molecular Cell, vol. 1, Apr. 1998, pp. 749–757.

Friedberg, E.C., Relationships between DNA Repair and Transcription, Annual Review of Biochemistry, vol. 65, Jan. 1, 1996, pp. 15–42.

Cook, Peter R., The Organization of Replication and Transcription, Science, vol. 284, Jun. 11, 1999, pp. 1790–1795.

Hoeffler and Roeder, Activation of Transcription Factor IIIC by the Adenovirus E1A Protein, Cell, vol. 53, Jun. 17, 1988, pp. 907–920.

Hoeffler et al., Activation of C–Jun Transcription Factor by Substitution of a Charged Residue in its N–Terminal Domain, Nucleic Acids Research, vol. 22, No. 7, 1994, pp. 1305–1312.

* cited by examiner

Primary Examiner—Carla J. Myers
(74) Attorney, Agent, or Firm—Townsend and Townsend and Crew LLP

(57) ABSTRACT

Certain transcription factors (enhancer binding proteins) significantly increase transcription rates from genes by nicking a single DNA strand in the vicinity of their DNA binding sites, thereby allowing RNA polymerase to gain access to the transcribed DNA strand by a process of "threading". DNA template nicking is a detectable and quantifiable byproduct indicative of transcriptional activation that can be used to design practical assays. These assays are used to determine which transcription factors (enhancer binding proteins) are actively catalyzing the transcription of a gene in any cell type, or in any cell in response to any drug or treatment. This group of transcription factors have a predictable molecular biological activity in addition to transcription activation, namely site-specific DNA strand cleavage.

16 Claims, 3 Drawing Sheets

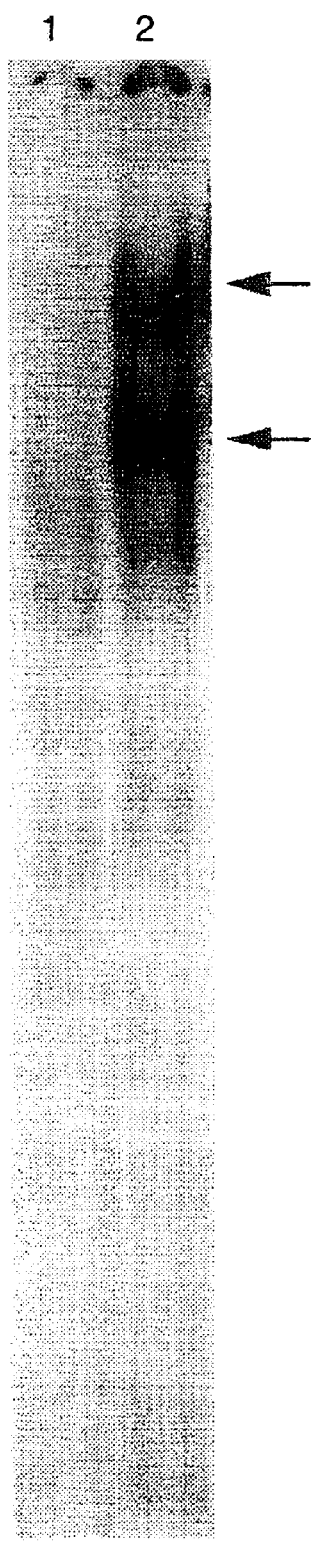
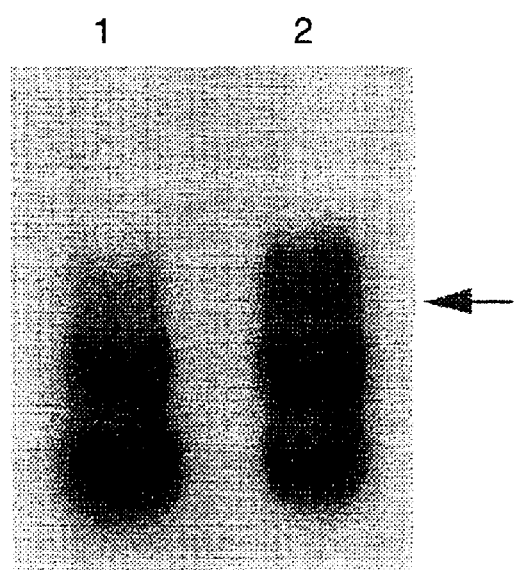
FIG. 5B
FIG. 5A

METHOD FOR DETERMINING TRANSCRIPTION FACTOR ACTIVITY AND ITS TECHNICAL USES

This application is the National Stage of International Application PCT/US99/23277, filed Oct. 6, 1999, which claims the benefit of U.S. Provisional Application 60/103,803, filed Oct. 9, 1998.

FIELD OF THE INVENTION

This invention relates to the field of molecular biology. In particular, this invention relates to transcription factors, methods of analyzing transcription factor activity, and to various technologies to which methods of analyzing transcription factor activity are related.

BACKGROUND OF THE INVENTION

Rapid advances in DNA technology have created a swell of new products and therapies through biotechnology, but the greatest gap in our ability to manipulate biological systems has been in the area of controlling gene expression. Specifically, despite our understanding and mapping of nearly all gene coding regions in human and several other species, we cannot 'decode' the DNA sequence that lies upstream of a gene, called the promoter. Enhancer binding proteins (subsequently referred to as transcription factors) bind to these regions, typically more than a dozen different ones bind to each and every gene promoter. How these factors work together to so precisely control the expression of genes has remained unsolved.

At stake is having predictive power of when a gene will be turned on or off based on assessment of the gene specific transcription factors present in a living cell at any given time, and in response to any treatments, including drugs. Also, the ability to alter gene expression or create promoters starting with individual transcription factor binding sites has been greatly impaired because one cannot 'read' what these factors are doing.

Currently, despite identifying many individual transcription factors, and in some cases having cloned them to know their exact amino acid sequences, how these factors help to catalyze transcription is not known. The current thinking is turning towards alterations in chromatin structure mediated by transcription factors possessing histone acetylase or deacetylase activity, yet most of the transcription factors positioned upstream of an eukaryotic gene do not have these activities.

Much work in the past in the transcription field has been focused on the role of so called 'general transcription factors' (GTFs), i.e., those factors required by all promoters to achieve gene transcription (see, for example, the work of Roeder, Sharp, Tjian, and Reinberg). The upstream binding transcription factors that control transcription rates have been presumed to interact with the components of the general transcription complex. In the dominant paradigm, a direct interaction between these upstream transcription factors and the GTFs presumably occurs by looping out of the intervening DNA. Yet during the decade that this model has dominated, it has not helped to illucidate further the role of upstream factors.

Prokaryotes (i.e., bacteria) have served as a model for eukaryotic transcription and it is presumed that the same set of transcription steps is likely involved in both systems. However, eukaryotes have many more genes regulated in more complex patterns and so may require a unique additional level of gene regulation. Specifically, eukaryotes employ transcription factors that enhance expression from distances of over a thousand base pairs away from the initiation site of transcription. Prokaryotes do not have this class of transcription factors and so do not provide a reliable model for understanding how eukaryotes regulate transcription.

There is thus a need to identify and characterize the molecular mechanism of transcription regulation and thereby explain how transcription factors work. Once this mechanism is determined, any of a number of assays for identifying and detecting transcription factors can be developed. The ability to manipulate the transcription of genes is necessary to overcome many obstacles in genetic engineering and gene therapy technology and will be required to cure several human diseases.

SUMMARY OF THE INVENTION

The invention relates to the discovery that certain transcription factors catalyze transcription by the creation of single-stranded nicks in one (and both strands in specialized cases) of the DNA strands of a gene template. This invention relates to the use of any means of detection of nicked DNA template or DNA nicking activity to assay transcription factor activity. This invention further relates to methods of identifying transcription factors by assaying DNA nicking activity. This invention further relates to methods of identifying consensus sequences related to the DNA nicking activity. Furthermore, this invention relates to the protein domains, and the DNA sequences encoding them, of transcription factors responsible for DNA nicking activity. This invention also relates to novel transcription factors identified by the methods of this invention.

This invention also relates to the use of an assay to detect strand breakage (nicking) of DNA in response to the binding of one or more transcription factors (enhancer binding proteins) to determine if these proteins are actively catalyzing gene transcription. These assays can be performed on any cell type, or in any cell or tissue in response to any drug, therapeutic agent or treatment. The DNA nicking assay may be a gel electrophoresis assay, an SI nuclease assay, a primer extension reaction, a polymerase chain reaction assay, a protein binding assay or any combination thereof. The analysis of nicking activity may be by extraction of the transcription factors to assess their activities on templates provided in vitro, or endogenous DNA templates can be extracted and amplified by PCR to determine the in vivo state of transcription factor induced nicks.

This invention further relates to the adaption of DNA nicking transcription assays to a 'DNA chip' or any solid or liquid matrix for rapid screening and analysis of transcription activity. In this matrix screening technique, double-stranded (ds) DNA oligonucleotides (or ds DNA fragments containing promoter element, i.e., transcription factor binding sites) containing DNA consensus sequences capable of specific binding with transcription factors are fixed to a matrix. The matrix is utilized as a support to identify specific oligonucleotide sequences, which are cleaved (nicked) in any solution containing transcription factors.

In the 'DNA chip' screening method of this invention, a DNA chip containing transcription factor DNA-binding consensus sequences may be incubated with a soluble cell extract containing representative transcription factors of any particular cell type in order to assay for transcription activity. This assay may be used in the evaluation of any DNA strand containing one or more DNA recognition sequences from a promoter region, or anywhere else in or surrounding a gene for the presence of nicks induced by the action of transcription factors. This method can be utilized as a means of determining which set of transcription factors and transcription factor binding sites work to increase gene transcription.

This invention is further directed to a database of transcription factors that actively nick DNA in any cell type, and in response to any set of conditions or treatments. The database may be utilized to predict which endogenous genes will be actively transcribed in certain cells based upon DNA sequence information of regions controlling the transcription of these genes. In one format of the invention, a useful database entry would be that a transcription factor, e.g., "X" is discovered to nick at a DNA binding site in a specific cell type. For example, fibroblast cells could be analyzed and the DNA sequence that transcription factors bind to and nick can be rapidly characterized because the induced nicks are easily detectable. A database of all transcription factor binding sites controlling each gene is used in conjunction with the cell type and condition database to realize full predictive power of the information.

This invention is further directed to a method of identifying transcription factors and their DNA binding sites utilizing a DNA nicking assay. In this invention, the database may be utilized to design, construct and utilize expression vectors capable of efficient expression in a particular cell type. Once identified, the DNA binding site for the transcription factor can be engineered into an appropriate expression vector to induce high levels of gene expression in cells.

This invention is further directed to the use of transcription factors to create single-stranded nicks in DNA in and around sites dependent upon the DNA consensus sequence for transcription factor binding. This use is analogous to restriction enzymes, which are currently used to cleave both strands of the DNA molecule in, and around the sites of their specific recognition sequences.

The unique set of transcription factors of this invention can be used to specifically cleave DNA. These factors are useful reagents for molecular biological manipulations.

This invention is further directed to the genetic engineering of transcription factors in order to alter their ability to nick DNA to yield more predictable patterns of behavior. In one format of the invention, some transcription factors must be phosphorylated on certain amino acids in order to exhibit DNA nicking activity. For these transcription factors, replacement or substitution of potentially phosphorylated amino acids with acidic residues, such as aspartic acid or glutamic acid, can allow the transcription factor to actively nick DNA even in the absence of phosphorylation.

This invention is further directed to the use of genetically engineered transcription factors for DNA nicking. The engineered transcription factors of this invention are more reliable than unmodified transcription factors.

The genetically engineered transcription factors of this invention may be utilized in vitro as molecular biology reagents or in vivo, by transformation, transfection or infection, into living cells to alter gene expression patterns. Cell lines containing genetically engineered transcription factors may be utilized in conjunction with expression vectors to produce various therapeutic agents, and similarly employed for use in gene therapy.

The genetically engineered transcription factors of this invention may be utilized in a variety of eukaryotic host organisms. Eukaryotes useful in the invention include fungi, insects, yeast, animals and plant cells. Although prokaryotes are used for expression of normal or genetically modified eukaryotic transcription factors, prokaryotes are not thought to be generally responsive to the class of transcription factors that induce nicks.

This invention is further directed to the broad use of DNA template nicking transcription factors to allow RNA polymerase access to the transcribed DNA strand by a process of "threading" the polymerase onto the transcribed strand. It is well known in non-specific transcription assays that unless eukaryotic RNA polymerase is offered a free DNA end it remains incapable of efficient transcription. The current paradigm is that GTF's substitute entirely for the need of a free end. In contrast, in this invention a free DNA end is critical to the control of eukaryotic gene regulation. In this invention, the threading of the polymerase onto a DNA strand is used as an assay endpoint. Assays measuring RNA polymerase entry onto the DNA template via a single-stranded nick, including measurable downstream events, such as RNA polymerase recognition of the TATA box, or other initiation of transcription elements or actual initiation of the RNA transcript are within the scope of this invention.

Presentation of a free DNA end is also a part of the proposed mechanism, where transcription factors not only nick the DNA template, but also remain bound to DNA to present a free DNA end to RNA polymerase. Such a mechanism would explain why a primary property of many transcription factors that enhance transcription is the presence of an acidic region, a so called acid blob. Positive charges on the 5' phosphate of a nicked end are repulsed by the positive charges of the transcription factor, resulting in the deflection of the free end, perhaps making it more accessible to RNA polymerase.

In this invention, the single-stranded cleavage of one strand of the DNA double helix by a transcription factor allows access to RNA polymerase and associated factors and creates an "on" state. In contrast whereas before the nicking event, RNA polymerase cannot enter the DNA strand and is in the "off" state. Thus the transcription factors of this invention can be utilized as 'gene transitors' responsible for turning on and off genes. The engineering of transcription factor DNA binding sites to create arrays of gene transitors for use in logic operations is also within the scope of this invention.

BRIEF DESCRIPTION OF THE DRAWINGS

This invention will be better understood by reference to the drawings, in which:

FIGS. 5A and 5B are photographs showing autoradiographs of a radioactively labeled dsDNA oligonucleotide after extraction from a gel shift experiment.

DETAILED DESCRIPTION OF THE INVENTION

I. Definitions

Figure 1:
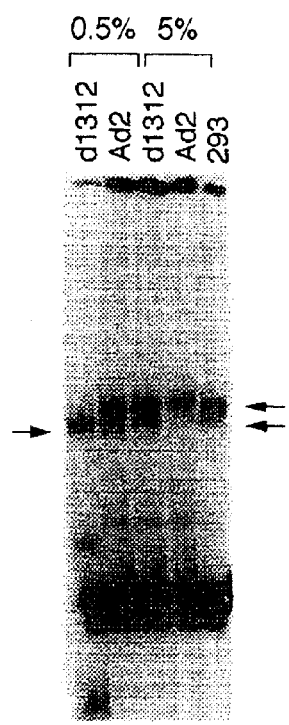
FIGS. 1A and 1B are photographs showing autoradiographs of radioactively labeled gel shift experiments for TFIIIC in nuclear extracts.

To ensure a complete understanding of the invention the following definitions are provided:

Transcription Factors:

Transcription factors are effector molecules that link second messenger pathways to gene expression pathways allowing a range of cellular responses to extracellular stimuli. Representative transcription factor sequences are available in public and private databases such as those produced by GenBank and Incyte Pharmaceuticals and the like. Transcription factors include, but are not limited to, proteins required for RNA polymerase recognition before transcription initiation of eukaryotic genes. A recombinant transcription factor can be a transcription factor encoded by a recombinant DNA comprising a transcription factor gene sequence or any subsequence thereof that exhibits transcription factor activity e.g., DNA nicking, DNA binding, or transcription modulating activity DNA template:

A DNA template refers to a DNA sequence comprising a site of direct or indirect interaction for one or more transcription factors. The DNA sequence may be one occurring naturally in nature, or may be a recombinant DNA sequence, i.e., one that is the product of in vitro or in vivo biochemical or genetic engineering manipulation. DNA isolated from cells, plasmids containing cloned DNA sequences, and oligonucleotides are all examples of DNA templates.

Contacting:

Contacting means to add to, to mix with, to flow over, to incubate with, or to co-transfect with, e.g., to introduce two compounds into a cell. The term also contemplates that the two or more compounds to be contacted can be co-expressed in vitro or in vivo.

Chip:

A chip, or "biological chip" as used herein, refers to a solid substrate, for example silicon or glass, having a surface to which one or more DNA, RNA or protein (peptide) templates are attached. One of skill in the art will understand that a biological "chip assay" can comprise the use of chip arrays or a plurality of biological chips within a single device or assay.

Detection reagent:

A "detection reagent" is a compound that can identify the presence or absence of a nicked DNA strand, e.g., by binding directly or indirectly to nicks in the DNA. Examples of detection reagents include, but are not limited to, proteins that preferentially bind to nicks in DNA, such as the X-ray repair cross complementing group 1 protein (XRCC1). Also included are antibodies that bind to proteins that bind preferentially to nicked DNA.

Detectable label:

A detectable label is a compound capable of being detected and/or measured by, for example, chemical, biochemical, photochemical, or spectroscopic means. Examples of detectable labels include radioactive isotopes, enzymes, fluorophores, chromophores, biotin conjugated antibody, chemiluminescent agents and the like. Labels may be directly detected through optical or electron density, radioactive emissions, non-radioactive energy transfers, or indirectly detected with antibody conjugates, etc.

Nicking transcription factor:

A nicking transcription factor is a transcription factor of the present invention, which has the ability to catalyze a single stranded nick in a double stranded DNA. A transcription factor of the invention may be a naturally occurring transcription factor, or a biochemically modified transcription factor, such as an in vitro phosphorylated nicking transcription factor. Also included in this definition is a recombinant nicking transcription factor, for example, a nicking transcription factor modified in vivo or in vitro by genetic manipulation to contain one or more amino acid substitutions.

Nicked DNA:

Nicked DNA is DNA in which one or more of the phosphodiester bonds linking the various nucleotide bases (adenine, guanine, cytosine and thymine) that make up the DNA sequence have been cleaved or broken.

DNA Nicking Activity:

DNA nicking activity is nucleotide bond breakage or cleavage in DNA sequences. DNA nicking activity can be measured by a variety of techniques such as (1) changes in electrophoretic mobility of nicked DNA on polyacrylamide and agarose gels; (2) determination of nicked DNA by protein binding assays with proteins that specifically bind nicked DNA; (3) enzyme assays with enzymes that move progressively along the DNA strand where the single-strand cleavage of a nick would terminate the reaction, and permit the identification of the location of the cleavage. Examples of such enzyme assays are S1 nuclease assays, primer extension reactions; Polymerase Chain Reaction (PCR) amplification reactions and DNA sequencing reactions.

In Vivo and In Vitro Nicking Assays:

Two categories of reactions designed to detect the DNA nicking activity are possible. In in vivo assays, the extent of nicking of endogenous DNA of the cell(s) is analyzed by methodology similar to that used for in vivo footprinting of proteins bound to DNA, for example ligation mediated PCR. These assays determine the state of the DNA as it is acted upon in the living cell. In in vitro assays, the transcription factors are extracted in their native states (most similar to their activities in vivo) and are reacted with DNA in vitro to assess their activity states are measured by nicking activity.

Taking into account these definitions, the present invention is directed to methods of analyzing transcription activity and methods of identifying transcription factors by measuring formation of single stranded and/or double stranded nicks or breaks in DNA sequence.

II. Detection of Nicking Activity

Although transcription factors bind DNA, it is not known that DNA is altered or nicked by interactions with a transcription factor.

In this invention, as illustrated in FIG. 1, a $^{32}$P end-labeled DNA fragment containing the DNA binding site for TFIIIC was incubated with a protein extract derived from the nuclei of a human fibroblast cell line (HeLa cells). The 129 nucleotide end-labeled VA gene fragment was incubated in a binding reaction with nuclear extracts prepared from cells maintained in either 0.5% or 5.0% serum and infected with either d1312 or Ad2. A nuclear extract from 293 cells was also analyzed. Equivalent volumes of extract (2 μl), derived from equivalent numbers of cells were assayed in standard binding reactions followed by electrophoresis.

The protein extract contains TFIIIC that is shown to bind to the DNA as one of two bands shown (arrows). (DNA not complexed with TFIIIC migrates faster on the polyacrylamide gel and is seen as the dark bands toward the bottom of the gel.) In cells known to be more transcriptionally active for polymerase III gene transcription there is more of an upper band species, whereas cells less active for polymerase III transcription there is more of the lower band species. Prior to my invention it was thought that the two bands differed from each other only in the character of the TFIIIC protein bound. In this invention I now conclude that the difference between the mobility of the two bands on the gel is primarily based upon the nicking of the DNA template in the upper band species, and that nicking is integral to the transcription factor (in this case TFIIIC) being able to catalyze transcription.

In a second experiment (FIGS. 2A and 2B) a $^{32}$P end-labeled DNA fragment containing the DNA binding site for TFIIIC was incubated with a protein extract derived from the nuclei of a human fibroblast cell line (HeLa cells) and the proteins were separated out chromatographically on a phosphocellulose column.

A HeLa cell nuclear extract (from cells maintained in standard 5.0% serum) was chromatographed on a phosphocellulose column. Fractions that eluted in the gradient between 0.40 and 0.70 M KCl were analyzed (FIG. 2A) by gel retardation assay using the labeled 129 nucleotide VA$_1$ fragment and (FIG. 2B) for TFIIIC activity in reconstituted in vitro transcription reactions using pVA$_1$ as the template DNA. Gel retardation assays were conducted by using 3.5 μl of each chromatographic fraction in standard binding reactions. Two series of in vitro transcription reactions were conducted by using 1.5 μl of each chromatographic fraction and 2.5 μl of the complementing phosphocellulose 0.35-M step fraction (containing TFIIIB and RNA polymerase III) derived from cells maintained in 0.5% serum and infected with d1312. The leftmost lane of each series contains only the 0.35-M step-complementing fraction to illustrate that in the absence of added TFIIIC no $VA_1$ transcription is observed.

Figure 2:
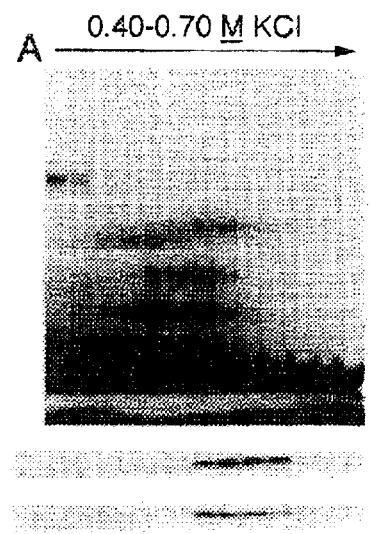
FIGS. 2A and 2B are photographs showing autoradiographs of radioactively labeled gel shift for TFIIIC.

The chromatography resulted in the separation of 2 forms of TFIIIC; one form when incubated with the DNA probe forms a lower band species (arrow on left) and the other form appears as the upper band species (arrow on right). In FIG. 2, Panel B shows which protein fractions have transcription activity in an in vitro transcription reaction. Only the fractions containing the upper band have transcriptional activity. Prior to my invention, since the TFIIIC proteins that form the upper and lower bands can be separated chromatographically, it was thought that only differences in the TFIIIC proteins cause the difference in migration of the upper and lower band complexes in the gel. Thus, a difference in the absolute size of the TFIIIC protein, or its charge, created the two distinct complexes. With this invention, I now conclude that the two bands also differ in mobility in the gel because of nicking of the DNA template. It thus follows from this experiment that only one form of TFIIIC possesses the ability to nick the DNA template, and thus has transcription activity.

Figure 3:
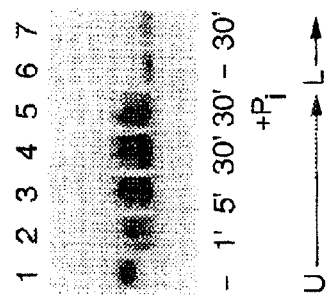
FIG. 3 is a photograph showing an autoradiograph of a radioactively labeled gel shift experiment.

In FIG. 3, a $^{32}$P end-labeled DNA fragment containing the DNA binding site for TFIIIC was incubated with a single protein fraction similarly derived as in the previous figure. A protein fraction containing TFIIIC that forms only the upper band complex was incubated with the DNA probe either alone (lane 1), or with a phosphatase for increasing number of minutes (lanes 2–4). The phosphatase enzyme can remove phosphates on certain amino acids within the TFIIIC protein. Prior to my invention, it was concluded that the dephosphorylated form of TFIIIC is smaller (lower molecular weight) than the phosphorylated form of TFIIIC and so the upper band is converted to the lower band due to the size of TFIIIC, and not due to effects on the DNA template. With this invention, I now conclude that the upper band form is nicked and, therefore, the dephosphorylated transcription factor can no longer nick the DNA probe, and so only the lower band forms. Conversely, phosphorylation of the transcription factor is necessary for it to be active in transcription and to provide nicking activity.

Figure 4C:
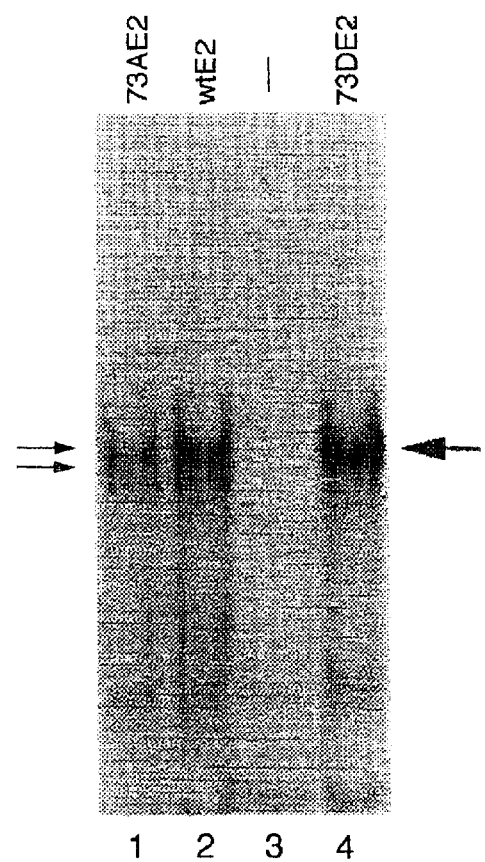
FIG. 4C shows the relative transcriptional activity of C-Jun/BPV-E2 fusion proteins.
Figure 4A:
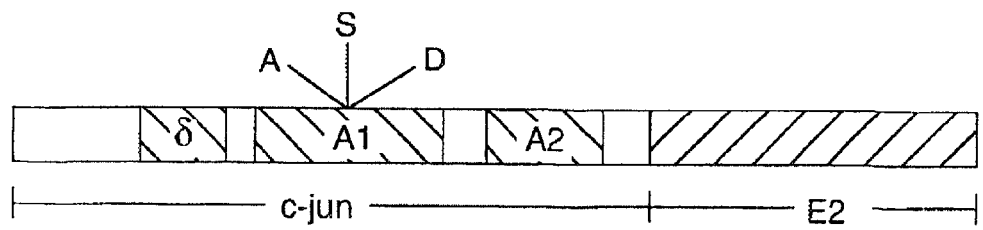
FIG. 4A is a diagram of C-Jun/BPV-E2 fusion proteins.

In FIG. 4, a $^{32}$P end-labeled DNA fragment containing the DNA binding site for BPV-E2 was incubated with a protein extract where the cells were transfected with an expression vector that makes a recombinant transcription factor able to specifically bind this DNA sequence. This factor c-Jun/BPV-E2 is a hybrid protein containing the C-terminal part of the BPV-E2 transcription factor (bovine papilloma virus E2 DNA binding domain) and the N-terminal part of c-Jun. It contains the transcriptional activation domain including amino acids Ser73 (and Ser63) that are phosphorylated in response to signal transduction (FIG. 4A). Gel shift assays were conducted using labeled oligonucleotide containing the DNA-binding site for the BPV-E2 protein. The oligonucleotides were incubated in whole cell extracts prepared from cells either not transfected or transiently expressing fusion proteins. The availability of DNA binding activity for the fusion protein either containing C-Jun (lane WtE2) or expressing the amino acid substitutions (lanes 73AE2 and 73DE2) was the greatest for the aspartic acid substitution (lane 73DE2).

Figure 4B:
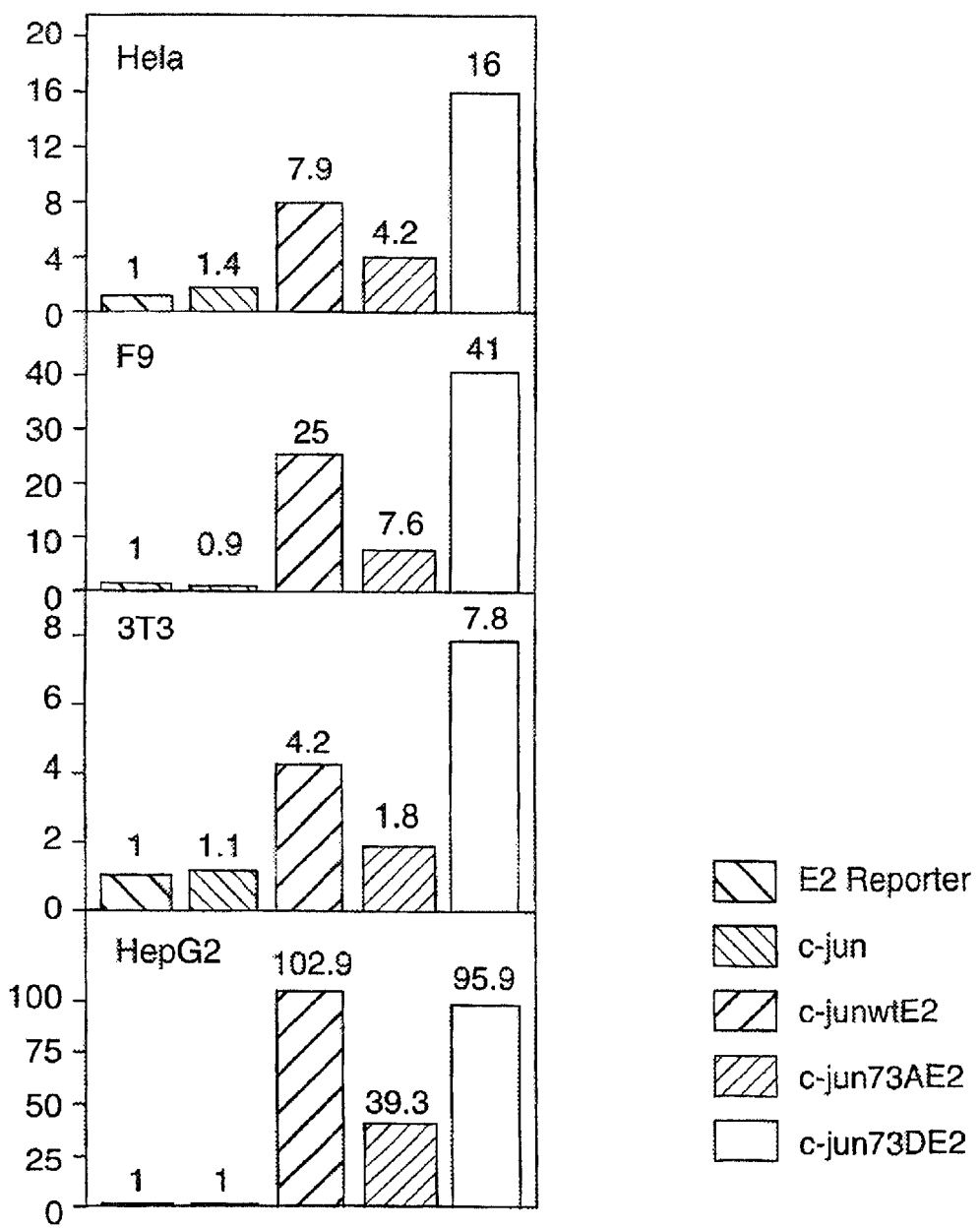
FIG. 4B shows the availability of C-Jun/BPY-E2 fusion proteins to bind to DNA by gel shift assays.

Since the DNA binding site for BPV-E2 is not recognized by any other transcription factors in the cells tested, only the transfected fusion protein c-Jun/BPV-E2 will bind to the $^{32}$P-labeled probe (FIG. 4B. no band visible in the negative control lane 3). Importantly, two bands are visible if either the normal c-Jun N-terminal end is used to create the fusion protein (wtE2, lane 2) or if an amino acid substitution of an alanine for Ser73 is made (73AE2 lane 1, marked with arrows on left of lanes). Thus, the phenomenon of two bands observed for TFIIIC in FIGS. 1–3 in the class III system is also observed for a derivative of c-Jun, in the class II system (enhancing catalysis of RNA polymerase II gene transcription i.e., making messenger RNA). The formation of an upper band corresponds to increased transcriptional activity as seen when an aspartic acid residue is substituted for Ser73 (73DE2 lane 4). In this case the upper band form predominates (marked with arrow on right) indicating that an acidic amino acid substitution containing a negative charge can substitute for the negative charge of a phosphorylated amino acid in creating an active transcription factor. The upper and lower bands are now understood in this invention to differ by nicking of the DNA probe (upper band) when the transcription factor is activated.

FIG. 4C shows the relative transcriptional activity of C-Jun/BPV-E2 fusion proteins. HeLa, F9, 3T3 and HepG2 cells were transiently transfected with 2 μg CAT (chloramphenicol acetyltransferase) reporter gene construct alone or with 2 μg of C-Jun or Jun/BPV-E2 expression vectors. E2CAT, which contains an E2 DNA-binding site was cotransfected to measure the transcriptional activation by each of the C-Jun constructs. CAT expression is shown as counts per minute of benzene-extractable [$^3$H]-monoacetylated chloramphenicol per μg extract protein.

Contransfection of a reporter gene construct driven by a promoter containing a BPV-E2 DNA binding site was used to measure transcriptional activity of the hybrid protein (FIG. 4C). Whereas an alanine substitution for Ser 73 had less transcriptional activity (c-Jun73AE2) than the wildtype (c-JunwtE2) an aspartic acid substitution (c-Jun73DE2) had greater transcriptional activity in all cell types tested.

These results indicate that genetically engineered transcription factors can be made that possess either greater or lesser ability to catalyze transcription, and create DNA nicks, than the normal wildtype factor. Also, creation of the fusion proteins c-Jun/BPV-E2 illustrates that a variety of DNA binding domains could be coupled to engineered transcriptional activation domains to get nicking at a new set of locations in the DNA sequence as determined by the DNA binding domain.

In FIG. 5A a $^{32}$P end-labeled DNA fragment containing either no known DNA binding site (lane 1) or the binding site for yet another transcription factor, CREB (cyclic AMP-responsive element binding protein) (lane 2), was incubated with a protein extract derived from the nuclei of HeLa cells under gel shift conditions, as previously. When electrophoresed in non-denaturing conditions two bands were observed to be unique for the CREB binding site. The separason of these two bands by migration difference in the gel was much greater than observed for other factors that showed active and inactive forms, and so these forms might not be related to each other in this way. To determine how the DNA template is effected by the binding of transcription factor, the DNA-protein complexes were cut out of the gel.

These gel slices were electroeluted in 1×TAE (0.04Mtris-acetate, 0.001M EDTA) buffer at 100 volts for 1 hr into a volume of about 200 μl in a dialysis bag with a 12,000–14,000 MW cut-off (Spectrum Medical Industries, Los Angeles). The eluent was made to 0.5% SDS, and 0.1 mg/ml proteinase K and digested for 15 min. at 56° C. An equal volume of a 1:1 mixture of phenol/chloroform was added and vortexed and centrifuged to extract any protein from the labeled DNA. The aqueous layer containing the DNA template was removed to a fresh tube, and 3 volumes of ethanol were added. A precipitate was allowed to form overnight at −20° C. and the tube was placed on dry ice for 15 min., and then spun full speed (14,000 rpm) in an eppendorf centrifuge for 15 min. The supernatant was decanted, and the pellet dried. The labeled DNA pellet was dissolved in standard DNA sample buffer (30% glycerol, 0.25% bromophenol blue, 0.25% xylene cyanol), and electrophoresed on a 15% polyacrylamide gel running in 1×TBE (0.09 M Tris-borate, 0.001M EDTA).

FIG. 5B shows the labeled template DNA extracted from the gel shift bands. The template extracted from the bottom band has 2 bands, as did the input template DNA, but the template extracted from the upper gel shift band has 3 bands, i.e., an extra band appears. This new band clearly indicates a change in the template DNA after incubation with an extract containing transcription factors. All trace of protein was removed from the DNA by this procedure, so the new band can only be formed by a change to the DNA template itself. Two properties of a nick template would cause it to move more slowly in the gel, as seen in this figure. Firstly, the breakage of phosphodiester bonds leaves a terminal phosphate with a positive change. The oligonucleotides used here were short, about 21 base pairs of dsDNA. The additional positive charge would make this fragment move less quickly toward the positive charge of the electrode in the bottom buffer chamber of the gel tank. Secondly, nicked DNA has an altered conformation that will allow it to bend at the location of the nick. This change in shape would alter its mobility in a gel. The changes in the DNA template after binding of transcription factors is consistent with nicking of the template.

Based upon these results, it is clear that transcriptional activity can be measured by measuring nicking activity in a host of assays.

III. General Methods of Detecting Transcriptional Activity

DNA nicking activity can be measured by a variety of techniques including: (1) electrophoresis assays to determine changes in electrophoretic mobility of nicked DNA on polyacrylamide and agarose gels; (2) determination of nicked DNA by protein binding assays; (3) SI nuclease assays; (4) primer extension assays; (5) PCR amplification reactions (6) DNA sequencing reactions and (7) hypersensitivity to strand cleavage.

In some of the DNA nicking assays, oligonucleotide primers are required to carry out the reaction. Generally, the design and synthesis of oligonucleotides of the invention follows conventional teachings. Preferably, oligonucleotides are synthesized on an automated, solid-phase DNA synthesizer using phosphoramidite chemistry (Beaucage et al. 1992; Caruthers, 1983), e.g. Model 392 or 394 DNA synthesizer (PE Applied Biosystems, Foster City, Calif.).

1. Electrophoresis Assays

Electrophoresis assays can readily be used to identify nicked and unnicked DNA to assay transcriptional activity.

Molecules of linear double-stranded DNA, which tend to become oriented in an electric field in an end-on position, migrate through gel matrices at rates that are inversely proportional to the $\log_{10}$ of the number of base pairs. Larger molecules migrate more slowly because of the greater frictional drag and because they worm their way through the pores of the gels less efficiently than smaller molecules.

A linear DNA fragment of a given size migrates through gels containing different concentrations of agarose at different rates. Thus, by using gels of different concentrations, it is possible to resolve a wide range of DNA molecules.

Superhelical circular (form I), nicked circular (form II), and linear (form III) DNAs of the same molecular weight migrate through agarose gels at different rates. The relative mobilities of the three forms depend primarily on the agarose concentration in the gel, but they are also influenced by the strength of the applied current, the ionic strength of the buffer, and the density of superhelical twists in the form I DNA. Under some conditions, form I DNA migrates faster then form III DNA; under other conditions, the order is reversed.

An unambiguous method for identifying the different conformational forms of DNA is to carry out electrophoresis in the presence of increasing quantities of ethidium bromide. As the concentration of ethidium bromide increases, more of the dye becomes bound to the DNA. The negative superhelical turns in form I molecules are progressively removed, the radii of the molecules increase, and their rate of migration decreases. At the critical free-dye concentration, where no superhelical turns remain, the rate of migration of form I DNA reaches its minimum value. As still more ethidium bromide is added, positive superhelical turns are generated, the DNA molecules become more compact, and their mobility increases rapidly. Simultaneously, the mobilities of form II and form III DNA decrease differentially due to charge neutralization and the greater stiffness imparted to the DNA by the ethidium bromide. For most preparations of form I DNA, the critical concentration of free ethidium bromide is in the range if 0.1 $\mu$g/ml to 0.5 $\mu$g/ml.

Because plasmid DNA typically has thousands of base pairs, and the nuclear extracts from cells being analyzed contain many transcription factors capable of binding at unforeseen locations, analysis of the conformation of plasmid DNA would work best when incubated with pure transcription factor preparations. In addition to seeing differences in plasmid DNA, short DNA fragments of about 100 base pairs, or less such as oligonucleotides, can migrate differently upon electrophoresis when nicked as compared to un-nicked DNA. The phosphodiester strand break creates a free charge, and the DNA can bend to a greater degree at the location of nicks, causing changes in migration on gels.

Electrophoresis assays can be readily used to separate and distinguish nicked from non-nicked DNA and as such, measure transcription activity and identify transcription factors. Such procedures are well known in the art as discussed above and as described in Sambrook, et al. *Molecular Cloning A Laboratory Manual* $2^{nd}$ Ed. (1989) Cold Spring Harbor Laboratory Press, which is hereby incorporated by reference.

2. Protein Binding Assays

Protein binding assays can also be used to measure DNA nicking activity and, therefore, transcriptional activity. Such procedures are well known in the art as described in Fried, M. and Crothers, D. M. (1981), Equilibria and kinetics of lac repressor operator interactions by polyacrylamide gel electrophoresis. Nucl. Acids Res. 9, 6505–6525 and Gamer, M. M. and Revzin, A. (1981), A gel electrophoresis method for quantifying the binding proteins to specific DNA regions. Applications to the components of the *E.coli* lactose operon regulatory system. Nucl. Acids Res. 9, 6505–3060, each of which is hereby incorporated by reference. DNA protein binding assays may consist of the minimal components necessary to permit DNA-protein interaction. The components of such assays will include a DNA template and a transcription factor protein (either native or recombinant).

The detection of DNA-protein complex formation involves determination of an electrophoretic mobility shift of labeled DNA on polyacrylamide gels containing, for example, 4% polyacrylamide (acrylamide:bisacrylamide, 30:0.8), 6.25 mM Tris base, 6.25 mM boric acid, 0.25 mM EDTA, (equivalent to ¼×TBE) electrophoresed at 120° volts (~20 mA at the beginning of the run). To see two bands for the binding of a single type of transcription factor preelectrophoresis of the gel is important. At a given voltage the amperage of the applied field increases soon after electrophoresis begins. The amperage needs to drop back from this spike, back to the starting amperage or slightly below. Secondly, the TBE buffer used in the gel and during electrophoresis works better if a 10×TBE stock solution is made up and allowed to age several months until significant white precipitate forms at the bottom of the bottle. Alterations in the formulation of the TBE buffer to mimic this change should work equivalently, including altering the ionic strength and/or the pH of the buffer.

Binding reactions can contain, for example, 4–8% glycerol, 0–4% ficoll, 7 mM $MgCl_2$, 20 mM Hepes-NaOH pH 7.9, 0.4 mM EDTA, 60–100 mM KCl, 1–4 µg poly (dl-dC) poly (dl-dC) in the presence of transcription factor protein (1–5 µg of either nuclear extract protein or chromatographic fraction, and DNA. The nuclear extract may be prepared as described below.

a. Nuclear Extract Preparation

Nuclear extracts are prepared by procedures well known in the art such as described in Dignam, J. D., Lebovitz, R. M., and Roeder, R. G. (1983) Accurate transcription initiation by RNA polymerase II in a soluble extract from isolated mammalian nuclei. Nucl. Acids Res. 11, 1475–1489 which is hereby incorporated by reference. In a modification of this procedure adapted to smaller numbers of cells growing on tissue culture dishes, cells are removed from a tissue culture plate (P-100) containing cells with the DNA target (most cell types including HeLa). The cells are washed twice with PBS (phosphate buffered saline). Eight hundred microliters of hypotonic buffer (for example, 10 mM Hepes pH 7.9, 1.5 mM $MgCl_2$ and 10 mM KCl) are then added to the cells. The cells are then incubated for 15 min. Next, the cells are scraped off into tubes and 4.8 µl NP–40 (non-ionic detergent) is added. The mixture is spun 5 min at 5 G. The supernatant is aspirated off and the nuclei resuspended in 50 µl lysis buffer containing 10 mM potassium (or sodium) phosphate pH 8.0 (a mixture of mono and dibasic mixture to yield pH 8.0), 0.5% NP40, 1.0 mM EDTA (pH 8.0) and 300 mM KCl. The mixture is then incubated for 30 min at 4° C. Next, the mixture is spun 10 min at 14,000 rpm (Eppendorf centrifuge) at 4° C. The supernatant containing the nuclear extract is removed to a fresh tube. Alternative methods for preparing extracts containing soluble transcription factors also work. For example, the cells can be directly solubilized in extraction buffer, without isolating nuclei first, to yield a whole cell extract.

b. Buffer Composition

Buffer composition is critical for analysis of DNA nicking activity. Phosphate buffer is preferred for extracting transcription factors in their active states. Phosphate buffer is preferred because transcription factors are often phosphorylated and can be dephosphorylated by phosphatase activity in the cell extracts if the phosphatase activity is not inhibited. The phosphate buffer serves as a competitive inhibitor to endogenous phosphatase. Other biological buffers not containing phosphate also work for the analysis of nicking activity. The addition of phosphatase inhibitors, such as sodium flouride at 50 mM, should help maintain the phosphorylation state of the extracted transcription factors.

c. Detection of Protein-DNA Complexes

The position of the labeled oligonucleotide is detected by appropriate methods (e.g., autoradiography for radioactive oligonucleotide). Mobility shifts are evidence of active nicking activity and thus active transcription activity, particularly when two forms of the DNA-protein complexes are formed that can be resolved by gel electrophoresis.

Other methods for detecting or separating DNA-protein complexes may be used, including UV crosslinking analysis, high performance liquid chromatography and phage display technology.

Formulation of protein-DNA complexes may be detected as a retention of labeled DNA (the label being detected by an appropriate methodology such as scintillation counting for radiolabeled DNA or flourometry from fluorescently labeled DNA) utilizing known affinity methods for protein immobilization. Such methods for protein immobilization are well known in the art and include biotin/streptavidin, nitrocellulose filtration, affinity chromatography, immunoaffinity chromatography, and related techniques.

Protein-DNA complex formation may also be detected as retention of labeled transcription factor (e.g. radioactively, fluorescently) utilizing known methods for immobilizing DNA.

3. SI Nuclease Assays

Nuclease SI degrades single stranded DNA or RNA to yield 5'-mono phosphate or oligonucleotides. Double stranded DNA, double stranded RNA and DNA:RNA hybrids are generally relatively resistant to the enzyme. However, moderate amounts of the enzyme will cleave double stranded nucleic acids at nicks or small gaps. As such, SI nuclease coupled with gel electrophoresis assays can be used to measure DNA nicking activity and hence transcription activity.

SI Nuclease assays are well known in the art. One example of an SI Nuclease assay is as follows. DNA containing a transcription factor binding site is end labeled and then preincubated with a protein extract containing the transcription factor activity to be tested. After nicking has occurred during this preincubation period the DNA is extracted with phenol/chloroform and ethanol precipitated. The DNA is subjected to S1 nuclease digestion is at 37° C. for 30 minutes in the presence of 100 ml S-1 mix (250 mM NaCl, 40 mM sodium acetate pH 5.5,1 mM $ZnSO_4$, 20 mg/ml denatured salmon sperm DNA and 2000 U/ml S1 nuclease). The reaction is terminated by adding sodium dodecyl sulfate (SDS) and EDTA to a final concentration of 0.2% and 20 mM, respectively, followed by phenol/chloroform extraction and precipitation with 0.3 M ammonium acetate and 50 % isopropanol. The precipitate is resuspended in 6 µl TE and 4 µl of stop buffer (95% formamide, 0.05% bromophenol blue, 0.05% xylene cyanol and 20 mM EDTA) and separated on a 6% polyacrylamide sequencing gel. Absence of the full-sized band, and the presence of smaller DNA fragments cleaved by S1, is evidence of nicking activity, as the SI nuclease has digested the full-length DNA at the position of the nick.

4. Primer Extension Reactions

Primer extension reactions can also be used to detect nicking activity and thereby assay transcriptional activity. The presence of a nick is required to Initiate the primer extension reaction. Detection of a primer extension product indicates the presence of a nick and, therefore, transcription activity.

Various primer extension assays are described in U.S. Pat. Nos. 5,952,202; 5,888,819 and 5,945,284, each of which is hereby incorporated by reference. Primer extension reaction procedures procedures involve the nicking of the DNA template by a transcription factor followed by extension reactions. A "primer" refers to an oligonucleotide capable of selectively annealing to a specified target nucleic acid and thereafter serving as a point of initiation of a primer extension reaction. A "primer extension reaction" refers to a reaction between a target/primer duplex and a nucleotide which results in the addition of the nucleotide to a 3'-end of the primer such that the added nucleotide is complementary to the corresponding nucleotide of the target nucleic acid.

The conditions for the occurrence of the template-dependent, primer extension reaction can be created, in part, by the presence of a suitable template-dependent enzyme. Some of the suitable template-dependent enzymes are DNA polymerases. The DNA polymerase can be of several types. The DNA polymerase must, however, be primer and template dependent. For example, E. coli DNA polymerase I or the "Klenow fragment" thereof, T4 DNA polymerase, 17 DNA polymerase ("Sequenase"), T. aquaticus DNA polymerase, or a retroviral reverse transcriptase can be used. RNA polymerases such as T3 or T7 RNA polymerase could also be used in some protocols. Depending upon the polymerase, different conditions must be used, and different temperatures ranges may be required for the hybridization and extension reactions.

Nucleic acids of interest may be analyzed by facilitating the analysis of the 3' terminal addition of terminators to a specific primer or primers under specific hybridization and polymerase chain extension conditions. Using only the terminator mixture as the nucleoside triphosphate substrate ensures addition of only one nucleotide residue to the 3' terminus of the primer in the polymerase reaction. Using all four terminators simultaneously ensures fidelity, i.e., suppression of misreading.

By specifically labeling one or more of the terminators, the sequence of the extended primer can be deduced. In principle, more than one reaction product can be analyzed per reaction if more than one terminator is specifically labeled.

By specifically tagging the oligonucleotide primer(s), or template(s) with a moiety that does not affect the 3' extension reaction yet permits affinity separation, the extension product(s) can be separated post-reaction from the unincorporated terminators, other components of the reagents, and/ or the template strand. Several oligonucleotides can be analyzed per extension reaction if more than one affinity agent is used.

a. Biotinylation of Oligodeoxynucleotides

In some circumstances, it is helpful to biotylate oligonucleotides to facilitate detection. Oligodeoxynucleotides, terminated at their 5'-ends with a primary amino group, may be obtained from Midland Certified Reagents, Midland, Tex. These may be biotinylated using biotin-XX-NHS ester (Clontech Laboratories, Inc., Palo Alto, Calif.), a derivative of biotin-N-hydroxysuccinimide. Typically, the oligonucleotide (9 nanomoles) are dissolved in 100 $\mu$l of 0.1 M $NaHCO_3/Na_2CO_3$ (pH 9), and 25 $\mu$l of N,N -dimethylformamide containing 2.5 mg biotin-XX-NHS-ester is added. The mixture is incubated overnight at room temperature. It is then passed over a 6 ml Sephadex G-25 column ("DNA grade"—Pharmacia) equilibrated with $H_2O$. Eluate fractions containing DNA are identified by mixing 4 $\mu$l aliquots with an equal volume of ethidium bromide (2 $\mu$g/ml) and the DNA-induced fluorescence is monitored with a UV transilluminator. Unreacted ester is detected by UV absorption at 220 nm. The tubes containing DNA are pooled, concentrated in a Centricon-3microconcentrator (Amicon), and passed over Sephadex again.

Inhibition of the binding of $^3$H-biotin to magnetic M-280 streptavidin Dynabeads (Dynal) can be used to assay quantitatively the extent of biotinylation of the oligonucleotides. Eppendorf tubes and pipet tips are siliconized. A known amount (5–10 pmoles) of biotin-labeled oligonucleotide in 10 $\mu$l 0.1 M NaCl is added to tubes containing 25 $\mu$l of 1:4 suspension of beads in 0.1 M NaCl. Increasing amounts of $^3$H-biotin (5–35 pmoles) in 20 $\mu$l of 0.1 M NaCl are added to the tubes and these are rotated again for one hour. Tubes are put on a, for example, Dynal MPC-E magnet to remove the beads from suspension, 10 $\mu$l aliquots of the supernatant are withdrawn, and the amount of radioactivity in these is measured using a Beckman LS 5000 TD liquid scintillation counter. Counts are compared to those from tubes to which no oligonucleotide has been added. Alternatively, for some primers, biotinylation is monitored by size fractionation of the reaction products using analytical polyacrylamide gel electrophoresis in the presence of 8 M urea.

b. Primer Extension/Termination Reactions.

Approximately five pmoles of 5'-biotinylated oligodeoxynucleotide template are mixed with approximately three pmoles of primer in 1×sequencing buffer (from Sequenase Version 2.0 kit, US Biochemical Corp.) (10 $\mu$l final volume). The mixture is incubated at 65° C. for 2 min, then allowed to cool to room temperature in order to anneal the primer and template. The solution containing the annealed template-primer is separated into two 5 $\mu$l portions, A and B, to which is added the following: Reaction A (for normalizing template concentrations)—0.5 $\mu$l of 100 mM dithiothreitol, 1 $\mu$l each of 10 $\mu$M DATP, dGTP, ddCTP, 0.5 $\mu$l of "Mn buffer" (from Sequenase Version 2.0 kit, US Biochemical Corp.), 0.5 $\mu$l of $^{35}$S-$\alpha$-thio-dTTP (10 mCi/ml, 1180 Ci/mmole) (Dupont-NEN), 1 $\mu$l of Sequenase (1:8 dilution, US Biochemical Corp.); Reaction B (for template-specific labeling of primer 3'-ends)—same additions as in Reaction A except the nucleotides used were ddCTP, ddGTP, ddTTP, and $^{35}$S-$\alpha$-thio-ddATP. Reactions are carried out for 5 min at 37° C. Control reactions omitting the primer or the Sequenase are also performed. Aliquots are removed and analyzed by electrophoresis on a 15% polyacrylamide, 8 M urea, DNA sequencing gel (see Maniatis, T., et al., Molecular Cloning. a Laboratory Manual, Cold Spring Harbor Laboratory (1982)). The gel is fixed in 10% methanol, 10% acetic acid, dried down onto Whatman's 3 MM paper, and exposed to Kodak X-Omat AR film. Alternatively, for purposes of analyzing the products by liquid scintillation counting, the biotinylated template or template-primer is bound to an excess of, for example, M-280 streptavidin Dynabeads (Dynal) before or after the Sequenase reaction (see above, "Biotinylation of oligodeoxynucleotides", for binding conditions). Beads are washed three times with 0.1 M NaCl to remove unincorporated label, then scintillation fluid is added and the radioactivity measured by liquid scintillation counting.

c. Generation of Templates From PCR Products

Polymerase chain reaction (PCR) reactions are carried out where one or the other of the amplification primers flanking the target stretch of DNA are biotinylated as described above. These primers (2 $\mu$mol final concentration) and the target DNA (up to 1 $\mu$g) are incubated with 2.5 units of Taq polymerase (Perkin Elmer/Cetus), 200 $\mu$M each of DATP, dCTP, dGTP, and dTTP, 10 mM Tris-HCl (pH 8.3), 50 mM KCl, 1.5 mM $MgCl_2$, and 0.01% gelatin (Sigma). Reaction mixtures were overlayed with paraffin oil and incubated for 30 cycles in Perkin Elmer/Cetus thermocycler. Each cycle consists of 1 min at 94° C., 2 min at 60° C., and 3 min at 72° C. Reaction products are purified by phenol/chloroform extraction and ethanol precipitation, then analyzed by ethidium bromide staining after electrophoresis on a polyacrylamide gel.

Approximately 5 $\mu$g of the PCR product is incubated with gentle agitation for 60 min with 50 $\mu$l of a suspension of prewashed, for example, M-280 Dynabeads in 0.1 M NaCl. The beads with the bound DNA (approximately 15 pmoles) are then incubated for 5 min at 25° C. with 0.15 M NaOH. Beads are washed once with 0.15 M NaOH to remove the unbiotinylated DNA strand, then washed three times with $H_2O$. The beads are resuspended in $H_2O$ and the strand bound to the beads via the biotin-streptavidin link is used as template for further primer extension reactions.

5. PCR Reactions

PCR reactions can be used to detect DNA nicking activity and thereby assay transcriptional activity. PCR amplification reactions are typically conducted in a reaction mixture composed of, per reaction: 1 $\mu$l genomic DNA containing a promoter from a gene of interest or a plasmid containing the promoter region; 10 $\mu$l each primer (10 pmol/$\mu$l stocks); 10 $\mu$l 10×PCR buffer (100 mM Tris.Cl pH8.5, 500 mM KCl, 15 mM $MgCl_2$); 10 $\mu$l 2 mM dNTPs (made from 100 mM dNTP stocks); 2.5 U Taq polymerase (Perkin Elmer AmpliTaq.TM., 5 U /$\mu$l) or Vent polymerase at a similar concentration; and $H_2O$ to 100 $\mu$l. The cycling conditions are usually 40 cycles (94° C., 45 sec, 55° C.; 30 sec; 72° C., 60 sec) but may need to be varied considerably from sample type to sample type. These conditions are for 0.2 mL thin wall tubes in a Perkin Elmer 9600 thermocycler. See, for example, Perkin Elmer 1992/93 catalogue for 9600 cycle time information. The target, primer length and sequence composition, among other factors, may also affect PCR parameters.

To detect nicks using PCR a single-sided PCR reaction can be conducted and used to map the location of nicks on each strand of the DNA containing promoter elements. One such protocol is termed "ligation-mediated PCR", that was developed for genomic sequencing and direct sequencing reactions, but is adapted in this invention for the identification and mapping of transcription factor induced nicks. Briefly, cleaved DNA is denatured and a gene specific primer (from a location downstream of where the DNA is being tested for the presence of nicks) is annealed. In first strand synthesis this primer is extended up to the nicked site creating a blunt site using a processive polymerase, such as Vent polymerase or Taq polymerase. A staggered linker is attached to the blunt end by DNA ligase, so that the 5' end of the extended DNA is ligated to the 3' end of the longer linker strand. The other shorter strand of the linker lacks a 5' phosphate and is therefore not ligated. A second primer near the first primer sequence and near the end of the boundaries of the sequence to be amplified is then annealed. After addition of a primer to the linker region the fragment is amplified by the polymerase through multiple rounds of PCR, eg. 18 rounds. This material can be analyzed directly by gel electrophoresis. Alternatively, the fragment can be radioactively labeled by several methods, including addition of a labeled 31 primer near the second primer that can be included in additional rounds of PCR to obtain a radioactively labeled fragment. The fragment is run on a sequencing gel near to a sequencing ladder created from the same primer to identify the exact location of the nick.

The use of PCR reactions is unique in that it is adaptable to both in vivo and in vitro nicking assays. Methods for extraction of genomic DNA are well known in the art, and can be found in Current Protocols in Molecular Biology, Supplement 20, 1992, which is hereby incorporated by reference. Briefly, in one sample protocol, cells grown in culture, or present in biopsied tissue are washed with phosphate buffered saline (PBS). For example, for a 15-cm plate of cells add1.5 ml of lysis buffer (300 mM NaCl, 50 mM Tris-Cl ph 8.0, 25 mM EDTA pH 80.2% (v/v) SDS, and 0.2 mg/ml proteinase K. Let plate stand for 5 min. at room temperature (rt). Transfer to 15 ml tube, and continue incubation at 37° C. for 3–5 hr., inverting every 30 min to mix. Add 1.25 volumes of buffered phenol, mix by inverting about 30 times. Centrifuge to separate phases. Remove aqueous to fresh tube. Add 1 volume of of by inverting 30 times, and centrifuge to separate phases. Remove aqueous to fresh tube. Repeat similar extractions with phenol/chloroform/isoamyl alcohol mix, and then with ethyl ether. Precipitate DNA with 1 volume of isopropyl alcohol. Pellet DNA, resuspend in TE, and reprecipitate in ethanol. DNA can now be used for ligation mediated PCR, as described above 6. DNA Sequencing Reactions DNA sequencing reactions can be used to detect nicking activity and, hence, transcription activity. Methods of DNA sequencing are well known in the art and include the enzymatic method of Sanger, et al. and the chemical degradation method of Maxam and Gilbert which are both described in Sambrook, et al. Other methods of DNA sequencing and DNA analysis are known and applicable to the present invention. These methods include the following, each of which is hereby incorporated by references.

U.S. Pat. No. 5,374,527 discloses the use of a low viscosity medium in capillary electrophoretic sequencing of DNA. The preferred medium is a solution containing between about 4 and about 7 weight percent linear polyacrylamide molecules. Detection is preferably performed by detection of fluorescent labels.

U.S. Pat. No. 5,405,746 discloses a method of sequencing DNA in which the terminus of one strand of a double-stranded DNA molecule is immobilized on a solid support, for example with a biotin-avidin system. In the method, the complementary DNA strands are separated. Next, the unbound strand is removed. Lastly, the fluorescent- or isotope-labeled Sanger extension products are prepared on the bound single stranded DNA molecules. One method for preparing the immobilized single-stranded DNA is by PCR amplification using primers with means such as biotin for attaching oligonucleotides, to produce directly immobilized single-stranded DNA prior to preparing Sanger extension products. The biotinylated DNA is immobilized on an avidin-agarose gel in a conventional slab format. Radiolabeled reaction products are detected after electrophoresis.

U.S. Pat. No. 5,484,701 discloses a process for isolating extension products of PCR amplification in which biotinylated primers are used in the PCR amplification procedure to produce biotinylated extension products. In the reaction, the extension products are immobilized by reaction with a biotinbinding protein such as avidin or streptavidin. Next, the immobilized products are separated from the liquid phase of the reaction and the immobilized complex is denatured with formamide. Sanger extension products are sequenced by electrophoresis of radiolabeled or fluorescent products on a gel.

U.S. Pat. No. 5,360,523 discloses a system for sequencing DNA by electrophoresis on conventional gel slabs or in gel-filled or buffer-filled capillary tubes, using infrared or near-infrared dyes to label the bases,. In the method, the bases are labeled with a laser diode to provide the excitation frequency. An automated scanning microscope is utilized for detection.

A. Woolley et al., "Ultra-High-Speed DNA Sequencing Using Capillary Electrophoresis Chips," Anal. Chem., vol. 67, pp. 3676–3680 (1995) discloses sequencing DNA by capillary electrophoresis in polymer-coated capillary channels microfabricated on a glass chip. Detection is performed by laser-induced fluorescence at visible wavelengths.

A. Cohen et al., "Separation and Analysis of DNA Sequence Reaction Products by Capillary Gel Electrophoresis," J. Chromatogr., vol. 516, pp. 49–60 (1990) discloses the use of capillary gel electrophoresis to separate DNA sequencing reaction products, with detection performed by laser-induced fluorescence.

Rolfs et al., "Fully-Automated, Nonradioactive Solid-Phase Sequencing of Genomic DNA Obtained from PCR," BioTechniques, vol. 17, pp. 782–787 (1994) discloses binding biotin-linked DNA to paramagnetic particles coated with streptavidin in the solid-state for the preparation of purified Sanger dideoxy sequencing ladders with fluorescent dye labeled primers.

Williams et al., "Single-Lane, Single-Fluor Sequencing using Dideoxy-Labeled, Heavy-Atom Modified Near-IR Fluorescent Dyes," SPIE, vol. 2386, pp. 55–65 discloses the use of capillary gel electrophoresis in DNA sequencing, in a polymer-coated silica capillary, with detection by near-infrared fluorescence. The different ddNTP's are labeled with the same dye, with molar concentrations varying in a ratio of 4:2:1:0. The bases are then distinguished from one another by fluorescence intensity measurements. Also disclosed is the alternative method of base-calling by measuring fluorescence lifetimes of certain heavy-atom-modified, near-infrared dyes, with similar absorption and emission spectra, but different fluorescence lifetimes.

The DNA sequencing methods described in these references may be employed for the detection of DNA nicking activity and the analysis of transcription.

7. Hypersensitivity to Strand Cleavage

Any of a variety of methods that generate random single stranded breaks in DNA can also be used to indicate the presence of nicks caused by the action of transcription factors. Such methods are, for example, used in the footprinting of proteins that bind to DNA. Not that these methods necessarily add much to the nicking induced by transcription factors, but these methods are appropriately designed to look at the state of the DNA template, and may indicate specific nicking along a DNA ladder created by the cleavage reagent. One such reagent is DNase I that will cut DNA randomly on each strand in the presence of $Mg^{2+}$. A footprint results when a DNA binding protein bound to the DNA template prevents DNase I from cutting. Interestingly, hypersensitive sites were sometimes noted within or just outside the boundaries of the protected footprint area, for unexplained reasons. If the transcription factor bound to DNA is in an active form it can cleave the DNA at a specific site that may reside within the consensus DNA binding sequence (or outside of it, as is also the case for restriction enzymes). Some of these hypersensitive sites may turn out to be nicking sites of activated transcription factors.

An early technique for indicating promoter region of genes in their in vivo context was sensitivity of these regions to double stranded cleavage by DNase. Although the clavage of the DNase is fairly random along the DNA, regions already nicked would be fully cleaved if additionally nicked with DNase, resulting in the observed phenomenon of DNase sensitivity for strand cleavage upstream of active genes.

IV. Use of Chip Technology to Detect Transcription Activity

The above methods of analyzing DNA nicking activity can be applied and utilized with chip technology.

Cells can be evaluated from any of the body's tissues, or the tissues of any organism for transcription activity using chip technology. Cells can be normal, or abnormal, derived from diseased tissue, including cancer, or before or after drug treatment. Cells can be isolated from any organism including insects, plants, animals, humans, algae, yeast and fungi. A protein extract of cell nuclei is prepared, as described above, containing representative transcription factors, as are present within the nuclei.

A. DNA Chips

A 'DNA chip' containing a population of double stranded DNA oligonucleotides each containing a potential DNA binding site for a transcription factor is bound to a known location on the chip. Such chips are described in U.S. Pat. No. 5,837,832, which is hereby incorporated by reference. The chip for the present invention is useful for double stranded DNA of complementary sequence containing unique sequence motifs that are recognized as binding sites by transcription factors. The protein extract containing the transcription factors is incubated with the DNA chip under conditions that allow both DNA binding and DNA strand cleavage or nicking. In the matrix screening technique of this invention, double-stranded DNA oligonucleotides containing DNA consensus sequences capable of specific binding with transcription factors are fixed to a matrix. The matrix is utilized as a support to identify specific oligonucleotide sequences that are cleaved (nicked) in any solution containing transcription factors.

In the 'DNA chip' screening method of this invention, a DNA chip containing DNA consensus sequences may be incubated with a soluble cell extract containing representative transcription factors of any particular cell type in order to assay for transcription activity. This assay may be used in the evaluation of any DNA strand containing one or more DNA recognition sequences from a promoter region, or anywhere else in or surrounding a gene for the presence of nicks induced by the action of transcription factors. This method can be utilized as a means of determining which set of transcription factors and transcription factor binding sites work to increase gene transcription.

The methods are particularly suited to automated high throughput transcription factor screening. In a preferred embodiment, the individual sample incubation volumes are less than about 500 µl, preferably less than about 250 µl, more preferably less than about 100 µl. Such small sample volumes minimize the use of often scarce candidate agent, expensive transcription complex components, and hazardous radioactive waste.

A variety of methods can be used to create a suitable DNA chip. For example, a glass slide can be used as a solid support, where the slide is cleaned and coated with polylysine, and dsDNA is spotted onto the slide into an array. Alternatively, VLSIPS technology developed by Affymetrix, Inc. can be used as described in a number of patents such as U.S. Pat. Nos. 5,861,242 and 5,945,384, each of which is hereby incorporated by reference. In the VLSIPS method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'—OH), is coupled to the activated areas of the support. The process can be repeated, using different masks or mask orientations and building blocks, to prepare very dense arrays of many different single stranded oligonucleotide probes. A complementary DNA strand must then be hybridized to the affixed ssDNA to yield dsDNA.

New methods for the combinatorial chemical synthesis of peptide, polycarbamate, and oligonucleotide arrays have recently been reported (see Fodor et al., 1991, Science 251: 767–773; Cho et al., 1993, Science 261: 1303–1305; and Southern et al., 1992, Genomics 13: 1008–10017, each of which is incorporated herein by reference). These arrays, or biological chips (see Fodor et al., 1993, Nature 364: 555–556, incorporated herein by reference), harbor specific chemical compounds at precise locations in a high-density, information rich format, and are a powerful tool for the study of biological recognition processes that could be utilized in the present application.

The DNA chips, prepared in any of a variety of these ways, are then incubated with nuclear extracts containing soluble transcription factors prepared from a broad sampling of cell types and tissues from a variety of eukaryotic organisms. In each case, the inclusion of a phosphatase inhibitor is important to maintaining transcription factor activity levels in the extracts, and can be provided by use of a buffer containing phosphate, as described above. The nuclear extracts are incubated with the DNA chips for several minutes to hours at 30° C. to 37° C. in order to allow cleavage of DNA strands by active transcription factors.

Detection of the DNA nicks can be accomplished by a variety of methods, and fall into four classes: proteins that bind to nicks, filling in of the nick with a detectable tag, detecting a stalled enzyme at the position of the nick, removal of a portion of the DNA strand separated from the rest of the strand by the nick achieved by denaturation.

a. Proteins (or Chemicals) That Bind to Nicks

A number of different proteins are capable of binding to nicks, and can be used to detect nicks. For example, several proteins involved in DNA repair will recognize and bind to nicks in DNA. These proteins (or chemicals) can be themselves coupled to a detector molecule, such as a radioactive tag, a colormetric tag, a fluorescent or phosphorescent tag, or they could be detected by a second molecule that will recognize them, such as an antibody. Binding candidates include all or part of the complex that recognize nicks in eukaryotic cells, that includes the X-ray repair cross complementation group 1 protein (XRCC 1), DNA ligase III, DNA polymerase, and PARP (Poly ADP Ribose Polymerase). XRCC1 has been shown to bind to nicked DNA itself, a property maintained by the N-terminal domain (NTD). Thus XRCC1, or XRCC1 NTD could be used to detect transcription factor induced nicks.

PARP was once thought to be a general transcription factor (TFIIC) because of its requirement in in vitro transcription reactions if the template DNA contained nicks, and TFIIH that couples transcription to DNA repair. TFIIH has multiple subunits and any of these individually may be appropriate including XPB, XPD and p62. Any proteins found to have high affinity for nicks can be used, such as helicases, topoisomerases, DNA ligases, or DNA polymerases. Potentially, single-stranded DNA binding proteins can also bind selectively to nicks, as are available from eukaryotes, prokaryotes, and their viruses or bacteriophages, respectively. The HU protein from E.coli has a KD of 8 nM for a 30-mer duplex DNA containing a nick, and so can also be used as a detector protein for transcription factor induced nicks.

The presence of the nick binding protein to a spot on the DNA chip can be detected in a variety of ways. The protein itself can be labeled with a radioactive tag, a colormetric tag, a fluorescent or phosphorescent tag. The protein can also detected by a secondary protein such as an antibody specific for the protein, or an antibody specific for a tag that is engineered to be contained in the nick detector protein. The antibody can contain the radioactive tag, a colormetric tag, a fluorescent or phosphorescent tag. Alternatively, a secondary antibody recognizing the first antibody could have these tags.

b. Filling In Nicks With a Detectable Tag

Several of the proteins mentioned above possess enzymatic activity for repair of the nicked DNA. For example, PARP will repair nicks in DNA by insertion of the terminal phosphate of ATP to reconnect the phosphodiester backbone. The inserted phosphate can be labeled to be detectable, by radioisotope tagging or by some other chemical modification. Likewise the nick may be repaired by TFIIH, a DNA polymerase or a DNA ligase, and in each case the repair reaction can insert a tagged molecule that can be detected as a positive signal in our assay.

Reaction intermediates can also be used to label the nicks. For example, DNA ligase incubated in the presence of nicked DNA and ATP will form a DNA-AMP complex at 0° C., observed to be more stable at pH 6.5 than at 7.0. A labeled group on the AMP can then be used to score the presence of the nick.

c. Detecting a Stalled Enzyme at the Position of Nicks

Enzymes that processively move along DNA will typically stall at the strand break of a nick, and this can be used to detect the nick itself. For example, DNA polymerase will stall at a nick during DNA synthesis because it cannot traverse the break in the phosphodiester backbone. A second detector molecule could detect the presence of the enzyme. Conditions can be used where only the stalled enzyme would remain bond to the template, such as a high enough ionic strength to dissociate an enzyme that is not stalled, while still allowing stalled enzymes to remain bound. Competitor DNA could also be a titrated ingredient of the wash solution for the detector DNA chip, allowing stalled enzymes to remain bound while other enzymes would be likely to become bound to competitor DNA, and so could be washed away thereby allowing detection of stalled enzymes.

d. Strand Separation of Unattached DNA Fragment Created by Nicks

If at least one of the strands of the dsDNA fragment containing the transcription factor binding site is attached to the solid support of the DNA chip then part of that strand will remain bound even after nicking of that strand has occurred. This opens up the opportunity to cleave off a detector molecule attached to the other side of the nick that would be no longer attached to the solid matrix. Heating, or other method of denaturation could be used to separate the two strands of the dsDNA, thereby allowing the fragment to be washed away. Likewise, if the non-nicked strand were also attached to the solid support then once the free fragment from the nicked strand is washed away a second labeled probe can be used to detect the unpaired strand, thereby detecting a nicked strand.

B Robotic Equipment

The methods of this invention are well suited for automation, especially computerized automation. Accordingly, a computer-controlled electromechanical robot preferably performs the method steps. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g., keyboard and/or mouse) and display (e.g., monitor) means for operator interfacing.

In a particular embodiment, the robotic station comprises a robotic arm with axially-positioned work stations including a working source plate station, a working pipette tip station, a working assay plate station, a liquid dispensing station, a wash station, a multiple channel pipettor station, a shaker station, a cooling station and a pipette tip storage station. In one format of the invention, the arm retrieves and transfers a microtiter plate or biological chip to a liquid dispensing station where measured aliquots of an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of scintillation cocktail is deposited in each designated well. Thereafter, the mount of label retained in each designated well is quantified.

DNA chips containing arrays of oligonucleotide probes can be used to determine whether a protein extract has DNA nicking activity. The array of probes comprises probes exactly complementary to the reference sequence, as well as probes that differ by one or more bases from the exactly complementary probes.

C. Database of Transcription Factors

This invention is further directed to a database of transcription factors that actively nick DNA in any cell type, and in response to any set of conditions or treatments. The database may be utilized to predict which genes will be actively transcribed in certain cells based upon DNA sequence information of regions controlling the transcription of these genes. In this invention, the database may be utilized to design, construct and utilize expression vectors capable of efficient expression in a particular cell type. In one format of the invention, a useful database entry would be that a transcription factor, e.g., "X" is discovered to nick at a DNA binding site in a specific cell type, for example fibroblast cells and the DNA sequence that it binds to and nicks can be characterized.

IV. DNA Nicking Activity Consensus Sequences

One of several methods can be used to determine which of the DNA oligonucleotides are cleaved. For example, a variety of proteins, or other molecules, are known to preferentially bind to nicks in the DNA, such as TFIIH or a single-stranded DNA binding protein. These proteins can be fluorescently tagged, or marked to facilitate detection. The chip is then 'read' to determine which DNA sequences were specifically nicked by active transcription factors. Since each transcription factor preferentially binds to only certain DNA consensus sequences, an inference is made between the sequence of the DNA oligonucleotide bound to the chip that was cleaved, and possible transcription factors known to bind to such a consensus sequence. Currently DNA chips are used to determine the presence of an RNA transcript, or as a means of DNA sequencing, based on hybridization between DNA strands. Here, DNA chips find a completely new purpose in assessing the set of transcription factors in active states, ready to catalyze transcription, in any given cell type from any organism type.

Any intact promoter region of any gene, or any region containing a binding site for a transcription factor can be assessed to determine when the factors are actively catalyzing transcription. The use of larger intact contiguous DNA strands may allow an assessment of which factors are working to activate a particular gene. Unlike DNA oligonucleotides that may be only large enough to contain one or two binding sites for transcription factors, a larger strand of DNA may allow a larger number of transcription factors to bind. The interaction of several factors together may also cooperate to create a nick on a gene to catalyze transcription. In this case more traditional methods of detecting the nick could be used, including S1 nuclease, primer extension reactions, PCR, or DNA sequencing reactions as discussed above.

V. Methods of Modulating Transcriptional Activity

Some transcription factors must be phosphorylated on certain amino acids in order to exhibit DNA nicking activity. For these transcription factors, replacement or substitution of potentially phosphorylated amino acids with acidic residues, such as aspartic acid or glutamic acid, can allow the transcription factor to actively nick DNA even in the absence of phosphorylation. Conversely, the substitution of an amino acid that cannot be phosphorylated, such as alanine would inactivate the transcription factor.

Amino acid sites within transcription factors that are phosphorylated in response to signal transduction are candidate sites for the control of transcriptional activity and associated DNA nicking activity. If the transcription factors have already been cloned, these sites can be mapped by incubating living cells with $^{32}$P (inorganic phosphate) while stimulating a certain signal transduction pathway that ends in the activation of a transcription factor. The factor will incorporate $^{32}$P at amino acids (Ser, Thr, Tyr) that may need to be phosphorylated in order for the transcription factor to be activated. The location of the phosphorylated amino acid can be determined by mapping the $^{32}$P labeled amino acid of a tryptic (or other protease) fragment, as typically resolved on either thin layer chromatography plates or on HPLC columns.

The amino acids that are phosphorylated in response to signal transduction are candidates for controlling transcriptional activation and thus DNA nicking activity. Acidic residues, either Asp or Glu, are genetically engineered to substitute for the amino acid substrates of phosphorylation. The thus modified transcription factors are tested for their ability to nick DNA. Overexpression of such engineered transcription factors could provide a whole new set of useful molecular biology reagents, creating enzymes that can effect single stranded cleavage of DNA at precise locations determined by the DNA sequence, much like restriction enzymes that are currently used to cut both strands of the DNA.

VI. Kits

The invention also provides kits useful for performing screens for activated transcription factors. Also provided are kits useful for assaying the level of transcriptional activity in an extract, cell or tissue. Kits of the invention comprise standardized reagents used to perform standardized methods for screening and measuring transcription by detecting DNA nicking activity. Kits may include, inter alia, containers or matrices for performing transcription assays, DNA templates for transcription factor binding or cleavage, suitable buffers for DNA binding and cleavage, reagents useful for detecting nicks in a DNA molecule, and written instructions.

VII. Biological Switches and Logic Operators

The identification of nicking activity as the key to transcription activity can be used as a biological switch. An analogy can be made between transcription factors of this invention and electronic transitors. A transitor is an electronic switch that controls the flow of electrons in a circuit. Similarly, these transcription factors of this invention function as 'gene transitors' controlling the flow of the enzymes (e.g. RNA polymerase) that lead to the expression of a gene. The invention therefore includes any use made of this class of transcription factors and their DNA consensus sequences as switching mechanisms, as constructed naturally, or in artificial assemblies, There are either of two positions, either the DNA is nicked or it is not, giving rise to the rudimentary element of computer logic. The definition of whether the switch is on or off can be determined by the state of the flow of molecules along the DNA. If RNA polymerase, another GTF, or any processive molecule able to travel down a DNA strand gains access to DNA through the nick then the nick is equivalent to being in the 'on' position. DNA repair enzymes can be made to reseal nicked DNA, so the switched can be turned off.

A subsequent potentially nicked region can be placed downstream of the first and present a potential barrier to the movement of the polymerase down the strand. Similar to two switches in series, the state of this biological logic gate is determined by whether the DNA is nicked at either location. Although one of the positions needs to be nicked to allow polymerase entry, nicking of the downstream site can create a potential barrier to the polymerase. In this case the definition of 'on' and 'off' changes, so that a second downstream site must kept whole to be on, and is turned off by a nick. Transcription factor binding sites can be arranged into logic assemblies by adjacent placement on a DNA strand. Use of these assemblies can be as computers, or other nanomachines.

VII. Relevant Prior Art

In addition to the prior art references discussed above, relevant patents, patent applications and publications include the following, each of which is hereby incorporated by reference. U.S. Pat. No. 5,143,854; WO 90/15070; WO92/10092, Hoeffler, W. K., Kovelman, R., and Roeder, R. G. (1988). Activation of Transcription Factor IIIC by the Adenovirus E1A Protein. Cell 41, 955–963. Hoeffler, W. K., Levinson, A. D., and Bauer, E. A. (1994). Activation of cJun transcription factor by substitution of a charged residue in its N-terminal domain. Nucl. Acids Res. 22, 1305–1312. Marintchev, A., Mullen, M. A., Maciejewski, M. W., Pan, B., Gryk, M. R., and Mullen, G. P. (1999) Solution structure of the single-strand break repair protein XRCC1 N-terminal domain. Nat Struct Biol 6(9), 884–893.

The invention now being fully described it will be apparent to one of ordinary skill in the art that many changes and modifications can be made thereto without departing from the spirit or scope of the appended claims.

What is claimed is:

1. A method of detecting eukaryotic nicking transcription factor activity comprising the steps of:

a) providing a DNA template comprising at least one binding region for a transcription factor;

b) contacting the DNA template with at least one eukaryotic nicking transcription factor; and c) detecting the presence or absence of a nick in the DNA template at or near the binding region of the eukaryotic nicking transcription factor, wherein the presence of a nick in the DNA template indicates nicking transcription factor activity.

2. The method of claim 1, wherein the transcription factor is in a nuclear cell extract.

3. The method of claim 1, further comprising the steps of:
   a) isolating the DNA template; and
   b) inserting the DNA template into a viral or plasmid vector and introducing the template into a cell.

4. The method of claim 1, further comprising the step of fixing the DNA template to a matrix.

5. The method of claim 4, wherein the matrix is a biological chip.

6. The method of claim 1 wherein the presence or absence of a nick in a DNA template is measured by determining the change in electrophoretic mobility of nicked DNA on an electrophoretic gel.

7. The method of claim 1 wherein the presence or absence of a nick in a DNA template is determined by a SI nuclease assay.

8. The method of claim 1 wherein the presence or absence of a nick in a DNA template is determined by a primer extension reaction.

9. The method of claim 1 wherein the presence or absence of a nick in a DNA template is determined by a polymerase chain reaction amplification reaction.

10. The method of claim 1 wherein the presence or absence of a nick in a DNA template is determined by a DNA sequencing assay.

11. The method of claim 1 wherein the presence or absence of a nick in a DNA template is determined by a protein binding assay.

12. The method of claim 1, wherein the eukaryotic nicking transcription factor comprises a site specific DNA binding transcription factor.

13. The method of claim 12, wherein the eukaryotic nicking transcription factor comprises an enhancer binding protein.

14. The method of claim 12, wherein the eukaryotic nicking transcription factor comprises a general transcription factor.

15. The method of claim 1, wherein the eukaryotic nicking transcription factor regulates the transcription of protein encoding RNA.

16. The method of claim 1, wherein the eukaryotic nicking transcription factor is selected from the group consisting of CREB, TFIIIC and c-jun.

* * * * *